(12) United States Patent
Yakumaru et al.

(10) Patent No.: US 6,531,143 B1
(45) Date of Patent: Mar. 11, 2003

(54) α-HYDROXY FATTY ACID DERIVATIVES AND EXTERNAL COMPOSITIONS CONTAINING THE SAME

(75) Inventors: Masafumi Yakumaru, Odawara (JP); Hiroko Nakatsugawa, Odawara (JP); Yoshiko Iwamoto, Odawara (JP); Takeshi Ikemoto, Odawara (JP)

(73) Assignee: Kanebo, Limited, Tokyo (JP)

( * ) Notice: Subject to any disclaimer, the term of this patent is extended or adjusted under 35 U.S.C. 154(b) by 0 days.

(21) Appl. No.: 09/701,532

(22) PCT Filed: May 27, 1999

(86) PCT No.: PCT/JP99/02831

§ 371 (c)(1), (2), (4) Date: Nov. 28, 2000

(87) PCT Pub. No.: WO99/62463

PCT Pub. Date: Dec. 9, 1999

(30) Foreign Application Priority Data

Jun. 4, 1998 (JP) ............................................. 10-155706

(51) Int. Cl.⁷ ........................ A01N 37/02; A01N 37/06; A61K 6/00; A61K 7/00; A61K 31/74; C07C 59/147; C07C 59/185

(52) U.S. Cl. ..................... 424/401; 424/78.03; 514/547; 554/121

(58) Field of Search ............................. 424/401, 78.03; 514/506, 675, 529, 547; 554/121

(56) References Cited

U.S. PATENT DOCUMENTS

| | | | | |
|---|---|---|---|---|
| 2,452,029 A | * | 10/1948 | Bruson et al. | 260/405 |
| 2,652,411 A | * | 9/1953 | Teeter et al. | 260/405 |
| 3,308,140 A | * | 3/1967 | Roe et al. | 260/404 |
| 4,469,635 A | * | 9/1984 | Peterson | 554/80 |
| 4,867,965 A | * | 9/1989 | Ciaudelli | 424/59 |
| 5,451,405 A | * | 9/1995 | Zhang et al. | 424/401 |
| 5,961,992 A | * | 10/1999 | Hardi et al. | 424/401 |
| 5,968,543 A | * | 10/1999 | Heller et al. | 424/425 |
| 5,989,533 A | * | 11/1999 | Deegan et al. | 424/70.28 |
| 6,020,489 A | * | 2/2000 | Franson et al. | 544/173 |
| 6,180,120 B1 | * | 1/2001 | Corey et al. | 424/401 |
| 6,180,669 B1 | * | 1/2001 | Tamarkin | 514/548 |

* cited by examiner

*Primary Examiner*—Srenni Padmanabhan
*Assistant Examiner*—Lauren Q. Wells
(74) *Attorney, Agent, or Firm*—Flynn, Thiel, Boutell & Tanis, P.C.

(57) ABSTRACT

An oily base, which has excellent stability, a low melting point and does not irritate the skin and an external composition which contains the oily base. The present invention is directed to an alpha-hydroxy fatty acid derivatives represented by the general formula (1):

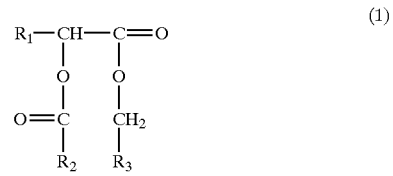

(1)

wherein $R_1$ represents a straight-chain or branched alkyl group having 10 to 24 carbon atoms, $R_2$ represents a straight-chain or branched alkyl group having 1 to 31 carbon atoms, and $R_3$ represents a straight-chain or branched alkyl group having 11 to 31 carbon atoms, and an external composition contains at least one of the derivatives.

16 Claims, 6 Drawing Sheets

α-HYDROXY FATTY ACID DERIVATIVES AND EXTERNAL COMPOSITIONS CONTAINING THE SAME

This Application is a U.S. National Stage Application of PCT/JP99/02831 filed May 27, 1999.

TECHNICAL FIELD

The present invention relates to novel alpha-hydroxy fatty acid derivatives, and external compositions containing the same.

BACKGROUND ART

For the purpose of minimizing water loss from the skin and hair and providing them with the smoothness, gloss or the like, oily bases have widely been used. Since these oily bases are applied to portions such as the skin or hair of the human body, the oily substances and body constituting substances preferably resemble each other in components and properties. The oily substances importantly exhibit neither irritation nor toxicity to the skin in view of the safety.

Therefore, there has hitherto been studied about a compound which has a resemblance to human sebum and trials of using ceramides contained exclusively in the human stratum corneum have recently been made (Japanese Examined Patent Publication (Kokoku) No. Hei 6-57651 and Japanese Examined Patent Publication (Kokoku) No. Hei 6-37429). Since a compound having a melting point in the vicinity of the body temperature or the skin surface temperature, or the melting point lower than that temperature, a trial of having an unsaturated bond in a molecular structure of the compound has been made. However, lipid having an unsaturated bond is generally easy to be oxidized by light and heat, moreover, its oxides sometimes induce strong irritation and toxicity to the skin. Therefore, in case such lipid is used in a skin external composition, it is necessary to protect from oxidization. On the other hand, since ceramide contained exclusively in the human stratum corneum is expensive and generally has a very high melting point and a high tendency to crystallize, its application is considerably limited at present.

It has been reported that wax diesters containing alpha-hydroxy fatty acids esterified with fatty acids and higher alcohols are present in the skin surface of animals such as cow, rabbit, cat and the like (T. Nikkari and E. Haahti, Biochim. Biophys. Acta. 164, 294–305 (1968), N. Nicolaides, H. C. Fu and M. N. A. Ansari. Lipids. 5, 299–307(1970)). These wax diesters contain, as principal components, alpha-hydroxy fatty acids having 14 to 22 carbon atoms, fatty acids having 14 to 28 carbon atoms and higher alcohols having 14 to 28 carbon atoms, but wax diesters composed of short-chain fatty acids having 2 to 6 carbon atoms have never been reported. It has never been reported to use wax diesters in external compositions.

An object of the present invention is to provide a novel oily base, which has excellent stability, low melting point, dose not irritate the skin and is superior feel in use, and an external composition contains the oily base.

DISCLOSURE OF THE INVENTION

The present inventors have studied intensively to attain the object described above and found that the alpha-hydroxy fatty acid derivative represented by the following general formula (1). Though the alpha-hydroxy fatty acid derivative is saturated compound, it has low melting point. And it dose not irritate the skin and is also superior in feel in use.

That is, the present invention is an external composition comprising one or more alpha-hydroxy fatty acid derivatives represented by the general formula (1):

(Chemical Formula 1)

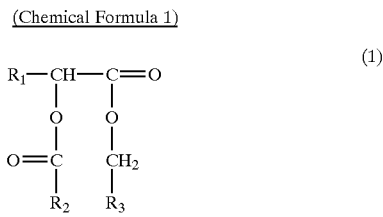

wherein $R_1$ represents a straight-chain or branched alkyl group having 10 to 24 carbon atoms, $R_2$ represents a straight-chain or branched alkyl group having 1 to 31 carbon atoms, and $R_3$ represents a straight-chain or branched alkyl group having 11 to 31 carbon atoms.

The present invention is also an alpha-hydroxy fatty acid derivatives represented by the general formula (2):

(Chemical Formula 2)

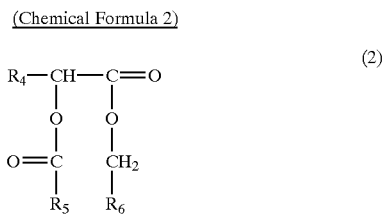

wherein $R_4$ represents a straight-chain or branched alkyl group having 10 to 20 carbon atoms, $R_5$ represents a straight-chain or iso- or anteiso-branched alkyl group having 1 to 5 carbon atoms, and $R_6$ represents a straight-chain or iso- or anteiso-branched alkyl group having 11 to 31 carbon atoms.

BEST MODE FOR CARRYING OUT THE INVENTION

Figure 1:
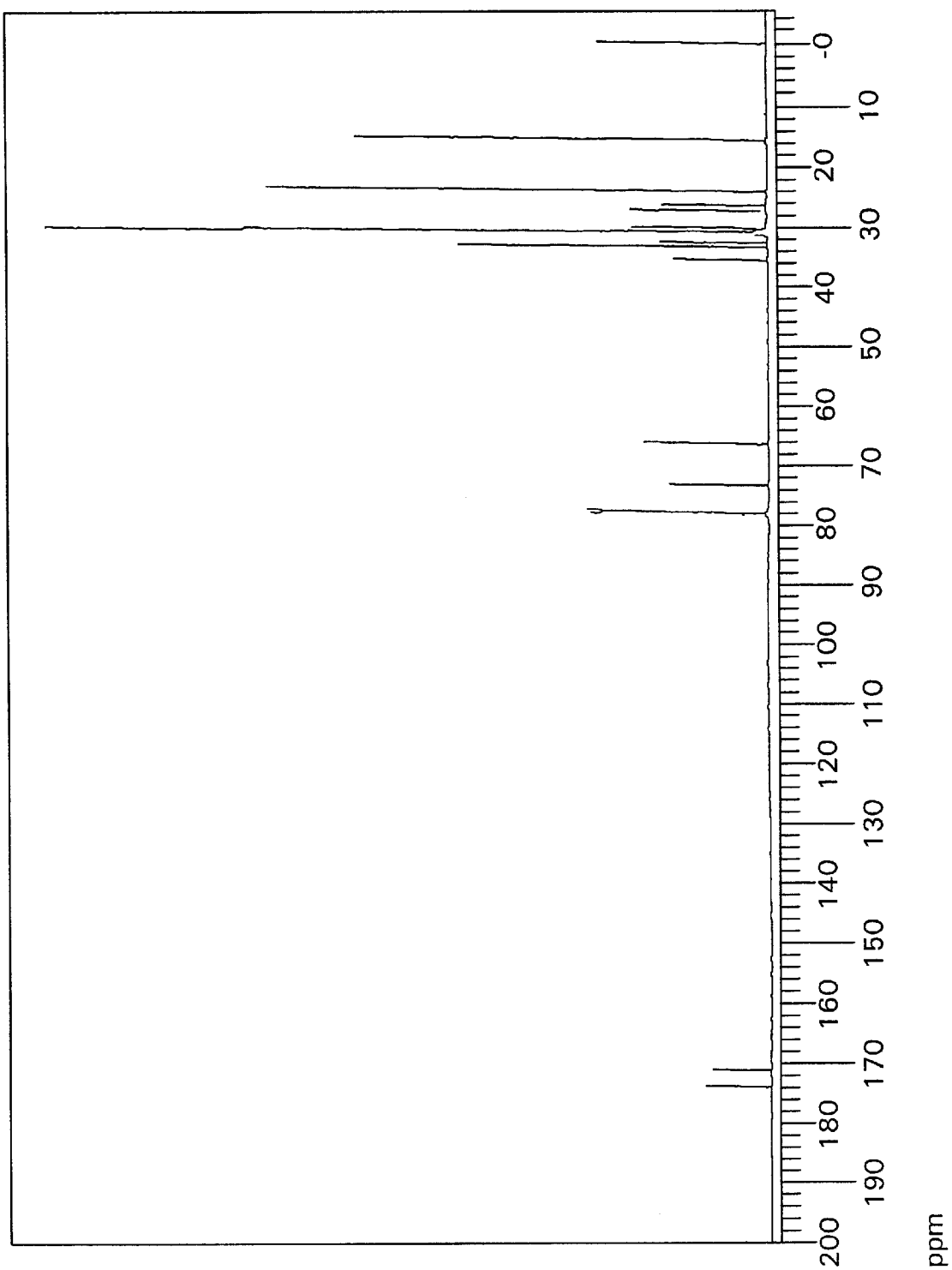
FIG. 1 is a $^{13}$C-NMR spectrum of 2-palmitoyloxypalmitic acid palmityl ester according to the present invention.

The embodiments of the present invention will be described in detail below.

The alpha-hydroxy fatty acid derivatives of the general formulas (1) and (2) of the present invention can be prepared by using an alpha-hydroxy fatty acid represented by the following chemical formula 3 or an alpha-hydroxy fatty acid derivative such as its methyl ester, a fatty acid represented by the following chemical formula 4 or fatty acid derivative such as an anhydrides and halides, and a higher alcohol represented by the following chemical formula 5 as raw materials according to a conventional procedure.

(Chemical Formula 3)

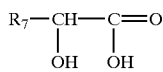

wherein $R_7$ represents a straight-chain or branched alkyl group having 10 to 24 carbon atoms (Chemical Formula 4)

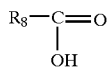

wherein $R_8$ represents a straight-chain or branched alkyl group having 1 to 31 carbon atoms (Chemical Formula 5)

wherein $R_9$ represents a straight-chain or branched alkyl group having 11 to 31 carbon atoms That is, the alpha-hydroxy fatty acid derivatives can easily be prepared by using an ordinary acidic catalyst and enzyme. If necessary, the alpha-hydroxy fatty acid derivatives can be used after purifying by deacidification, decoloring and deodorization according to a conventional method. In some cases, the alpha-hydroxy fatty acid derivatives may be contained unreacted alpha-hydroxy fatty acid, fatty acid, higher alcohol, and alpha-hydroxy fatty acid monoalkyl ester as an intermediate.

The alpha-hydroxy fatty acid derivatives (1) and (2) according to the present invention can be extracted from Cashmere goat's fur by using an organic solvent. If necessary, the alpha-hydroxy fatty acid derivatives can also be used after purifying by a conventional method. Those, which are, present on the surface animal's fur such as cow, rabbit, cat and the like do not correspond to the alpha-hydroxy fatty acid derivative (2) and is contained in the derivative (1).

The alpha-hydroxy fatty acid derivative according to the present invention obtained by the above procedure can be used in skin care compositions such as lotions, milky lotions, creams, packs, face washes, foundations, lipsticks, and bath preparation; and hair care compositions such as shampoos, rinses, hair treatments, and hair creams. The alpha-hydroxy fatty acid derivative can be used in conventional cosmetics, quasi-drugs and drugs.

In the external composition according to the present invention, the amount of the alpha-hydroxy fatty acid derivative is preferably used within a range from 0.1 to 60.0% by weight (hereinafter described as "wt %") based on the total weight in view of the effect and economical reason.

In the external composition according to the present invention, there can be used components that are conventionally used in cosmetics, quasi-drugs and drugs. Specific examples of the component include fats and oils, dyes, perfumes, antiseptics, surfactants, pigments, antioxidants, cheleting agents, ultraviolet absorbers, ultraviolet scattering agents, polymeric viscosity modifiers, inorganic salts, polyhydric alcohols, vitamins, higher alcohols, vegetable extracts and the like. As used herein, the term "external composition" includes a hair care composition and a skin care composition.

As the surfactant, for example, any of cationic, anionic, nonionic, amphoteric and other surfactants can be used. Examples of the cationic surfactant include quaternary ammonium salts such as aliphatic amine salt, quaternary ammonium salt, alkyltrialkyleneglycol ammonium salt, alkyl ether ammonium salt, pyridinium salt, imidazolinium salt, benzalkonium salt and the like. Examples of the anionic surfactant include carboxylates such as acylaminate, alkyl ether carboxylate, and fatty acid salt; sulfonates such as N-acylmethyltaurine salts and alpha-olefin sulfonic acid salts; sulfates such as alkyl sulfate and fatty alkanolamide sulfate; and phosphates such as polyxyethylene alkyl ether phosphate and fatty amide ether phosphate. Examples of the nonionic surfactant include polyhydric alcohol fatty esters or polyhydric alcohol alkyl ethers, such as sorbitan fatty acid ester, sucrose fatty acid ester, and ethylene glycol monofatty acid ester; polyoxyethylene ethers such as polyoxyethylene alkyl ether, polyoxyethylene alkyl phenyl ether, polyoxyethylene cholesterol, and polyoxyethylene polyoxypropylene alkyl ether; ether esters such as polyoxyethylene monofatty acid ester, polyethylene glycol difatty acid ester, polyoxyethylene sorbitan fatty acid ester, polyoxyethylene sorbitol fatty acid ester, polyoxyethylene castor oil, polyoxyethylene alkyl ether fatty acid ester, and polyoxyethylene methyl glucoside fatty acid ester; and nitrogen-containing derivatives such as alkylamine oxide, polyoxyethylene alkylamine, and alkyldiethanol amide. Examples of the amphoteric surfactant include glycine type surfactants, aminopropionic acid type surfactants, carboxybetaine type surfactants, sulfuric acid type surfactants, phosphoric type surfactants, and carboxylic acid type surfactants such as sulfobetaine type surfactant. Examples of the other surfactant include fluorine surfactants; silicone surfactants such as polyether-modified silicone and amino-modified silicone; and natural surfactants such as saponin and lecithin.

Examples of the polyhydric alcohol include ethylene glycol, diethylene glycol, triethylene glycol, polyethylene glycol, propylene glycol, dipropylene glycol, polypropylene glycol, glycerin, diglycerin, polyglycerin, 3-methyl-1,3-butanediol, 1,3-butylene glycol, saccharides and the like.

The higher alcohols to be used may be natural or synthetic higher alcohol, and may be straight-chain, branched, saturated or unsaturated. Specific examples thereof include isostearyl alcohol, octyl dodecanol, hexyl decanol, lauryl alcohol, myristyl alcohol, stearyl alcohol, oleyl alcohol, behenyl alcohol, cetanol and the like.

The following Examples further illustrate the present invention in more detail, but the present invention is not limited by these Examples.

EXAMPLE 1

Preparation of 2-palmitoyloxypalmitic acid palmityl ester

To 27.2 g of 2-hydroxypalmitic acid and 24.2 g of cetyl alcohol, 100 ml of n-hexane was added and the mixture was dissolved with heating. Then, 4 g of a neutral thermo-stabile lipase obtained by immobilizing on an acrylic resin (immobilized lipase, Novozym 435 manufactured by Novo Nordisk A/S) was added and reacted at 60° C. for six hours while removing water formed during the reaction. Then, the immobilized lipase was removed by filtration and the solvent was removed under reduced pressure to obtain a light yellow wax.

The resulting wax was purified by silica gel column chromatography (developing solvent:hexane/ethyl acetate= 10/1) and a fraction having Rf value of 0.57 in TLC analysis (developing solvent:hexane/ethyl acetate=10/1) was concentrated to obtain 38.5 g of a white solid. The formation of 2-hydroxypalmitic acid palmityl ester was confirmed by a signal at 175.5, 70.5 and 65.7 ppm observed in the measurement of $^{13}$C-NMR.

25.7 g of 2-hydroxypalmitic acid palmityl ester by the method described above and 13.7 g of palmitoyl chloride was reacted by a conventional method in the presence of pyridine. After the reaction, chloroform was added and the product was washed with water under acidic conditions. Then, the solvent was removed under reduced pressure to obtain a light yellow wax. The resulting wax was purified by silica gel column chromatography (developing solvent:hexane/ethyl acetate=20/1) and a fraction having Rf value of 0.86 in TLC analysis (developing solvent:hexane/ethyl acetate=10/1) was concentrated to obtain 34 g of a white solid. The formation of 2-palmitoyloxypalmitic acid palmityl ester as the alpha-hydroxy fatty acid derivative of the present invention was confirmed by a signal at 173.3, 170.6, 72.3 and 65.3 ppm observed in the measurement of $^{13}$C-NMR, as shown in FIG. 1. Using JNM-LA 400 (400 MHz) [manufactured by JEOL Ltd.] as a measuring apparatus, CDCl$_3$ as a measuring solvent and TMS as a certified reference material, the measurement of $^{13}$C-NMR was conducted. Hereinafter, the measurement of $^{13}$C-NMR was conducted by the same procedure.

EXAMPLE 2

Preparation of 2-isobutyryloxymyristic acid-(18)-methylicosanyl ester

To 26.1 g of methyl 2-hydroxymyristate and 31 g of 18-methylicosanol, 200 ml of n-hexane was added and the mixture was dissolved with heating. Then, 3 g of an immobilized lipase (Novozym IM, manufactured by Novo Nordisk A/S) was added and reacted at 60° C. for five hours while removing methanol formed during the reaction. Then, the immobilized lipase was removed by filtration and the purification was conducted in the same procedures as in Example 1 to obtain 37.6 g of a white solid. The formation of 2-hydroxymyristic acid-(18)-methylicosanyl ester was confirmed by a signal at 175.5, 70.5 and 65.7 ppm observed in the measurement of $^{13}$C-NMR.

26.3 g of 2-hydroxymyristic acid-(18)-methylicosanyl ester prepared by the method described above and 6.0 g of isobutyryl chloride, the preparation and purification were conducted by the same procedure as in Example 1 to obtain 26.5 g of a white solid. The formation of 2-isobutyryloxymyristic acid-(18)-methylicosanyl ester as the alpha-hydroxy fatty acid derivative of the present invention was confirmed by a signal at 176.5, 170.6, 72.2 and 65.3 ppm observed in the measurement of $^{13}$C-NMR.

EXAMPLE 3

Preparation of 2-acetyloxystearic acid-(18)-methylnonadecanyl ester

In the same procedures as in Example 2, except that methyl 2-hydroxymyristate was replaced by methyl 2-hydroxystearate and 18-methylicosanol was replaced by 18-methylnonadecanol and, furthermore, isobutyryl chloride was replaced by acetyl chloride, 2-acetyloxystearic acid-(18)-methylnonadecanyl ester was prepared. The formation of 2-acetyloxystearic acid-(18)-methylnonadecanyl ester as the alpha-hydroxy fatty acid derivative of the present invention was confirmed by a signal at 170.46, 170.44, 72.5 and 65.3 ppm observed in the measurement of $^{13}$C-NMR of the white solid obtained in the above preparation.

EXAMPLE 4

Figure 2:
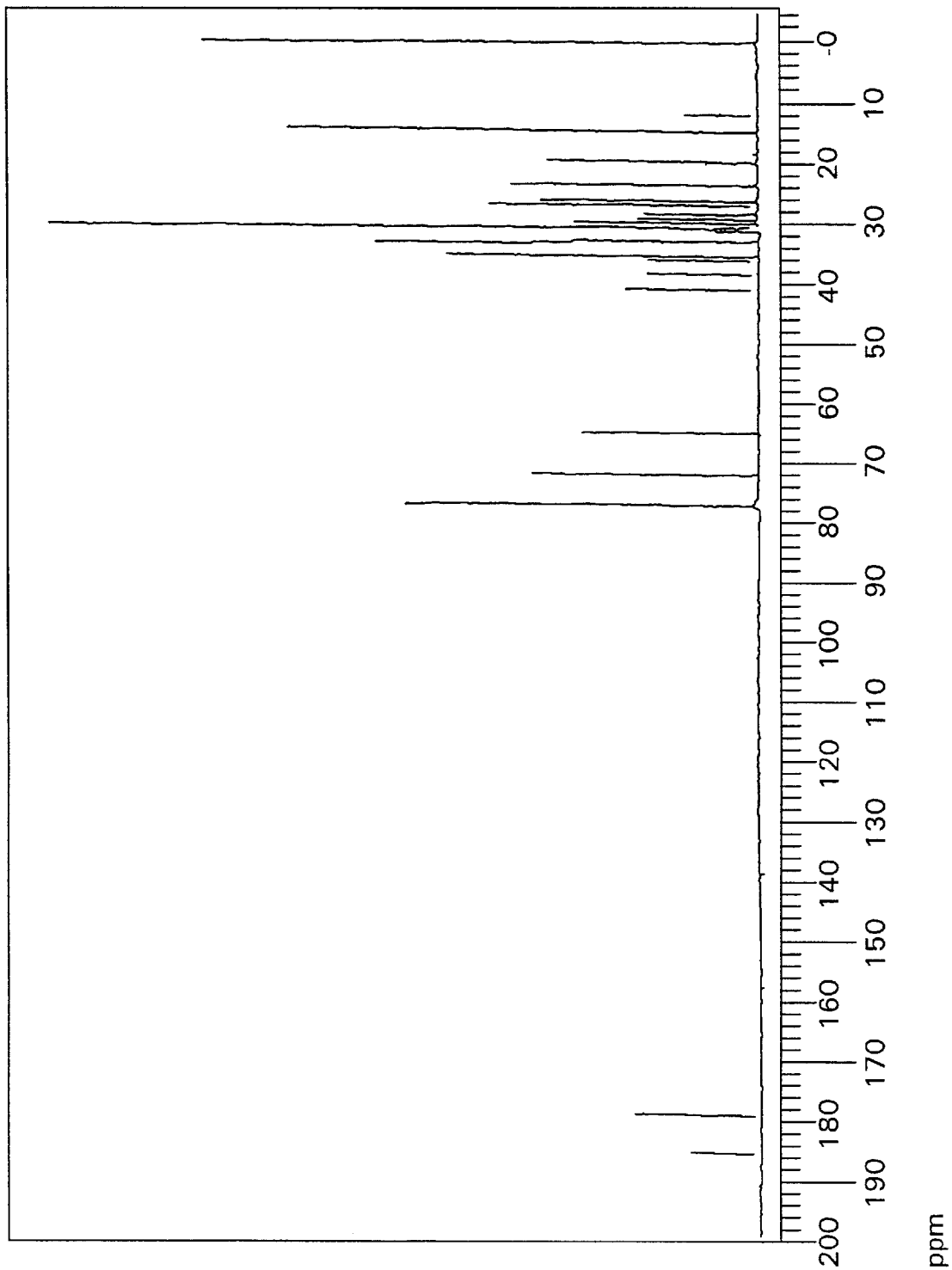
FIG. 2 is a $^{13}$C-NMR spectrum of 2-isobutyryloxy long-chain fatty acid (14–25) long-chain branched alcohol (12–31) ester according to the present invention.

Preparation of 2-isobutyryloxy long-chain fatty acid (14–25) long-chain branched alcohol (12–31) ester In the same procedures as in Example 2, except that a alpha-hydroxy fatty acid methyl ester esterified from long-chain alpha-hydroxy fatty acid (14–25) [YOFCO-FE-ALF manufactured by Nippon Fine Chemical Co., Ltd.] by using a conventional method was used in place of methyl 2-hydroxymyristate, a long-chain branched alcohol reduced from a long-chain branched fatty acid (12–31) [YOFCO-FE-NH manufactured by Nippon Fine Chemical Co., Ltd.] by using a conventional method was used in place of 18-methylicosanol, 2-isobutyryloxy long-chain fatty acid (14–25) long-chain branched alcohol (12–31) ester was prepared. The formation of 2-isobutyryloxy long-chain fatty acid (14–25) long-chain branched alcohol (12–31) ester as the alpha-hydroxy fatty acid derivative of the present invention was confirmed by a signal at 176.5, 170.6, 72.1 and 65.3 ppm observed in the measurement of $^{13}$C-NMR of the transparent liquid obtained in the above preparation, as shown in FIG. 2.

EXAMPLE 5

Preparation of 2-isobutyryloxypalmitic acid palmityl ester

In the same procedures as in Example 1, except that palmitoyl chloride was replaced by isobutyryl chloride, 2-isobutyryloxypalmitic acid palmityl ester was prepared. The formation of 2-isobutyryloxypalmitic acid palmityl ester as the alpha-hydroxy fatty acid derivative of the present invention was confirmed by $^{13}$C-NMR.

EXAMPLE 6

Preparation of 2-acetyloxypalmitic acid palmityl ester

In the same procedures as in Example 1, except that palmitoyl chloride was replaced by acetyl chloride, 2-acetyloxypalmitic acid palmityl ester was prepared. The formation of 2-acetyloxypalmitic acid palmityl ester as the alpha-hydroxy fatty acid derivative of the present invention was confirmed by $^{13}$C-NMR.

EXAMPLE 7

Preparation of 2-isovaleryloxylauric acid lauryl ester

In the same procedures as in Example 2, except that methyl 2-hydroxymyristate was replaced by methyl 2-hydroxylaurate and 18-methylicosanol was replaced by lauryl alcohol and, furthermore, isobutyryl chloride was replaced by isovaleryl chloride, 2-isovaleryloxylauric acid lauryl ester was prepared. The formation of 2-isovaleryloxylauric acid lauryl ester as the alpha-hydroxy fatty acid derivative of the present invention was confirmed by $^{13}$C-NMR.

EXAMPLE 8

Preparation of 2-long-chain branched fatty acid (12–31) oxypalmitic acid palmityl ester In the same procedures as in Example 1, except that an acid chloride synthesized from long-chain branched fatty acid (12–31) [YOFCO-FE-NH manufactured by Nippon Fine Chemical Co., Ltd.] by using a conventional method was used in place of palmitoyl chloride, 2-long-chain branched fatty acid (12–31) oxypalmitic acid palmityl ester was prepared. The formation of 2-long-chain branched fatty acid (12–31) oxypalmitic acid palmityl ester of the present invention was confirmed by $^{13}$C-NMR.

EXAMPLE 9

Preparation of Wax Diesters from Cashmere Goat's Fur

After 1 kg of Cashmere down obtained by removing guard hair, dirt and scurf from raw fur was washed with running water for 24 hours and sufficiently dried, was extracted with 2 liters of acetone with stirring for two hours. The extract was filtered and concentrated under reduced pressure to obtain 35 g of Cashmere lipids extract. The Cashmere lipids extract was purified by silica gel column chromatography (developing solvent:hexane/ethyl acetate= 10/1) and a fraction having Rf value of 0.5 in TLC analysis (developing solvent:hexane/ethyl acetate=10/1) was concentrated to obtain 10.5 g of a transparent liquid wax diesters fraction.

Figure 3:
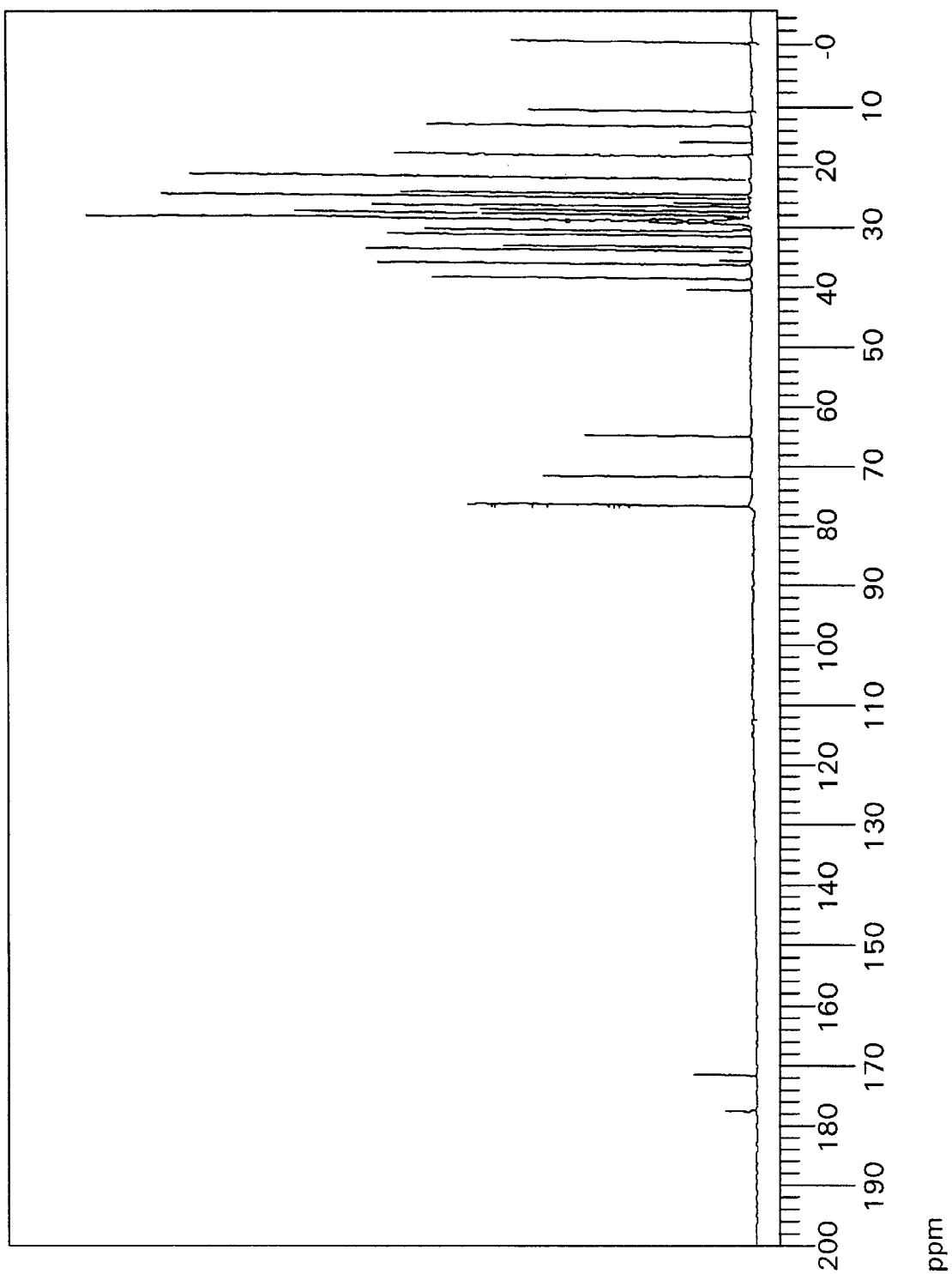
FIG. 3 is a $^{13}$C-NMR spectrum of the wax diesers fraction from Cashmere goat's fur(alpha-hydroxy fatty acid derivative mixture) according to the present invention.

The formation of the fraction as the alpha-hydroxy fatty acid derivative of the present invention was confirmed by a signal at 176.5, 170.6, 72.2 and 65.3 ppm observed in the measurement of $^{13}$C-NMR, as shown in FIG. 3.

Furthermore, the wax diesters fraction was saponified and methylated by conventional methods and then analyzed by gas chromatography. As a result, it has been found that the alpha-hydroxy fatty acids contain alpha-hydroxy palmitic acid as a principal component and have 12 to 20 carbon atoms. Furthermore, the alpha-hydroxy fatty acids were saturated, straight-chain compounds contained small amounts of iso- or anteiso-branched chain compounds. On the other hand, the fatty acids were straight-chain, or iso- or anteiso-branched saturated fatty acids having 2 to 6 carbon atoms, principally isobutyric acid. The higher alcohols were straight-chain, or iso- or anteiso-branched saturated higher alcohols having 12 to 25 carbon atoms , principally 18-methylicosanol and 18-methylnonadecanol. That is, the wax diesters of Cashmere were compounds corresponding to the general formula (2).

Figure 4:
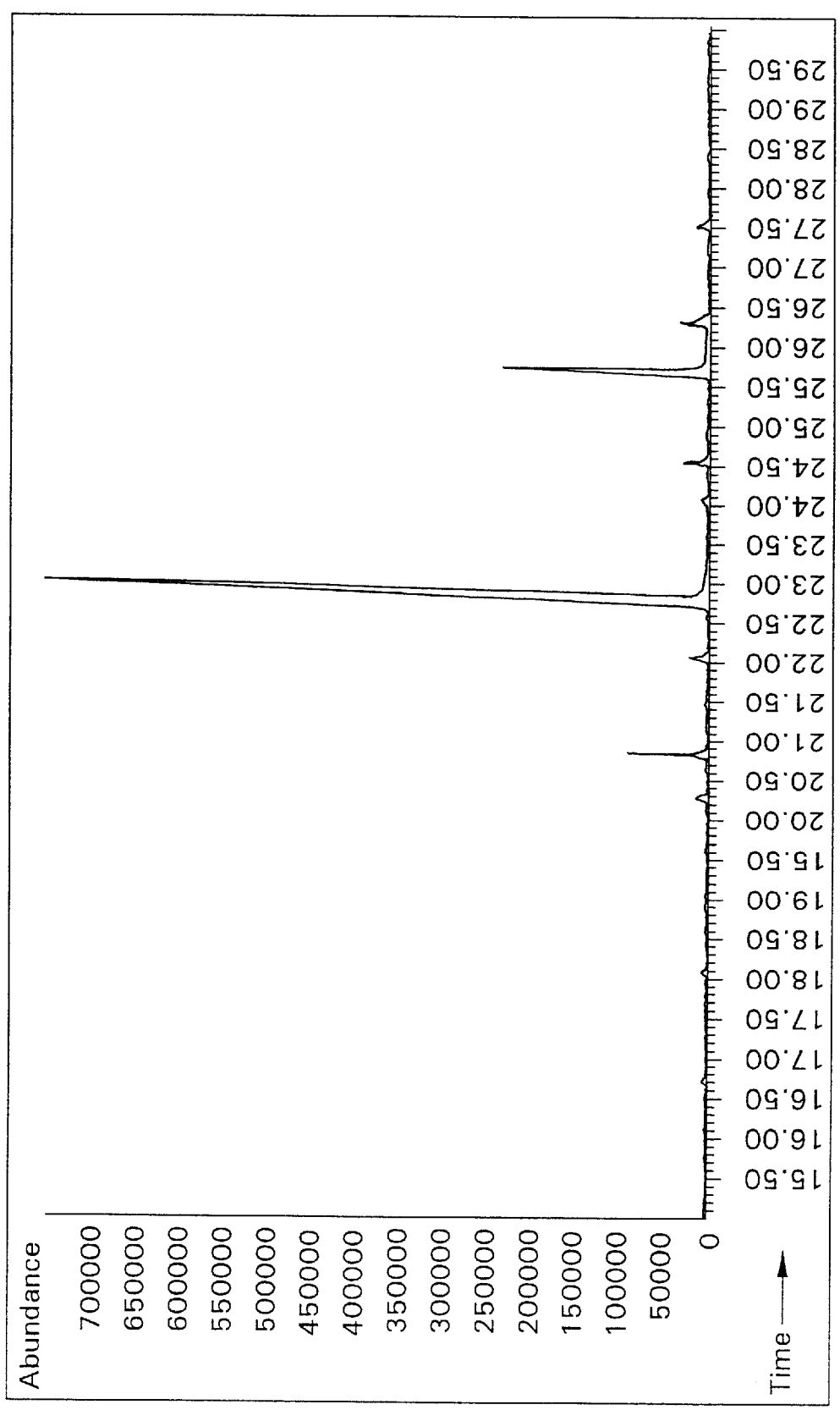
FIG. 4 is a gas chromatogram of alpha-hydroxy fatty acids obtained from the wax diesters of Cashmere.
Figure 5:
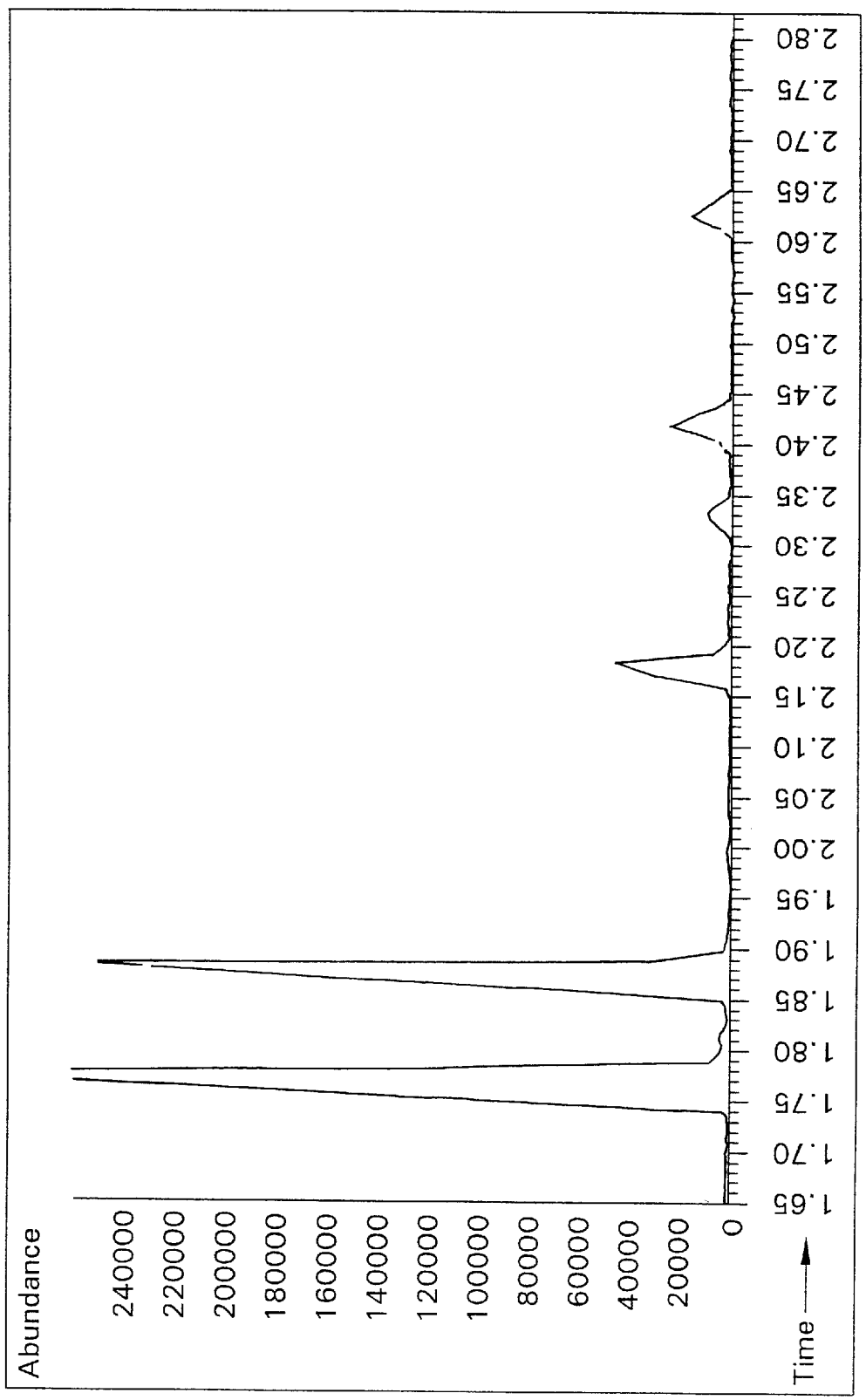
FIG. 5 is a gas chromatogram of fatty acids obtained from the wax diesters of Cashmere.
Figure 6:
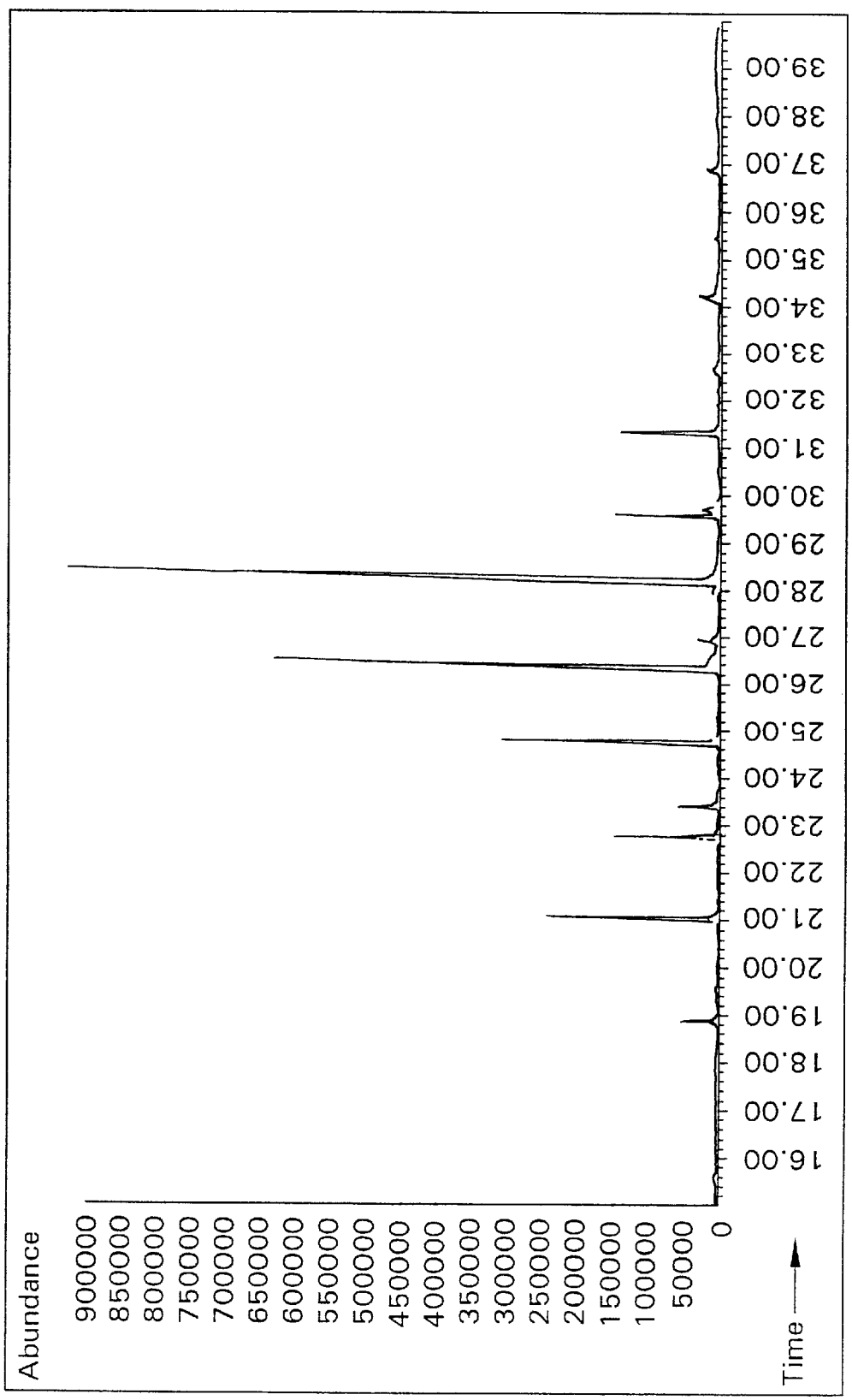
FIG. 6 is a gas chromatogram of higher alcohols obtained from the wax diesters of Cashmere.

The respective gas chromatograms of the alpha-hydroxy fatty acids, fatty acids and higher alcohols are shown in FIG. 4, FIG. 5 and FIG. 6. The analyses were conducted under the following conditions.

Alpha-hydroxy fatty acids, Higher alcohols
Gas chromatograph: 5890 series II manufactured by Hewlett-Packard
Column: DB-1, 30 m×0.25 mm I.D., 0.25 μm (manufactured by J. and W. Scientific)
Temperature programmed: 100° C. (1 min) to 300° C. (10 min) at 5° C./min
Detector: MSD Fatty acids
Gas chromatograph: 5890 series II manufactured by Hewlett-Packard
Column: HP-INNOWAX, 30 m×0.25 mm I.D., 0.25 μm (manufactured by Hewlett-Packard)
Temperature programmed: 70° C. (3 min) to 100° C. at 2° C./min 100° C. to 250° C. (5 min) at 5° C./min
Detector: MSD The melting point of the alpha-hydroxy fatty acid derivatives of the present invention, measured by differential scanning calorimetry (DSC, EXTER6000 System manufactured by Seiko Instruments Inc.), is shown in Table 1. 2-Palmitoyloxypalmitic acid palmityl ester, 2-isobutyloxy long-chain fatty acid (14–25) long-chain branched alcohol (12–31) ester, 2-isobutyryloxypalmitic acid palmityl ester and 2-acetyloxypalmitic acid palmityl ester were obtained in Example 1, Example 4, Example 5 and Example 6, respectively. For comparison, glyceryl tripalmitate (manufactured by Tokyo Chemicals Industry Co., Ltd.), cetyl palmitate (manufactured by Funakoshi Co., Ltd.), ceramide 2 (manufactured by Cederma) and ceramide 3 (manufactured by Gist-brocades), that have hitherto been used in cosmetics, quasi-drugs and drugs, were used. The results are also shown in Table 1. A final peak of the DSC curve was taken as the melting point.

TABLE 1

| Name of compounds | Melting point (° C.) |
|---|---|
| 2-palmitoyloxypalmitic acid palmityl ester | 52.5 |
| 2-isobutyloxy long-chain fatty acid (14-25) long-chain branched alcohol (12-31) ester | 2.0 |
| 2-isobutyryloxypalmitic acid palmityl ester | 28.3 |
| 2-acetyloxypalmitic acid palmityl ester | 35.1 |
| Wax diesters of Cashmere | −0.8 |
| Glyceryl tripalmitate | 64.1 |
| Cetyl palmitate | 52.8 |
| Ceramide 2 | 106.8 |
| Ceramide 3 | 125.3 |

As described in Table 1, the alpha-hydroxy fatty acid derivatives according to the present invention had noticeably lower melting points than that of ceramide, and the ordinary oily base having the same molecular weight. And the melting points were closer to the body or the skin surface temperature. As is apparent from these results, the alpha-hydroxy fatty acid derivative according to the present invention is superior in physical properties for lipid to be used in external compositions such as skin or hair composition.

Among alpha-hydroxy fatty acid derivatives according to the present invention, the melting points of 2-isobutyryloxypalmitic acid palmityl ester, 2-isobutyryloxy long-chain fatty acid (14–25) long-chain branched alcohol (12–31) ester or 2-acetyloxypalmitic acid palmityl ester wherein the chain length of the substituted fatty acid is short [$R_2$ in the general formula (1) or $R_5$ in the general formula (2)], were noticeably lower than that of 2-palmitoyloxypalmitic acid palmityl ester and are closer to the body temperature or skin temperature. That is, the alpha-hydroxy fatty acid derivative has particularly excellent physical properties for oily base used in the external composition.

As the safety test, irritation to the skin was examined by the following method. Each sample of the alpha-hydroxy fatty acid derivatives obtained in the Examples prepared by dissolving in olive oil in the concentration of 50 wt % and an adhesive plaster for patch test was impregnated with 1 ml of the sample. The adhesive plaster was put on the facies medialis brachii of 20 subjects for 24 hours. Irritation was evaluated 24 hours after removing the patch. The result was rated by percentage of positive subjects who showed a clear erythema. The results are as shown in table 2.

TABLE 2

| Name of samples | Positive percentage (%) |
|---|---|
| 2-palmitoyloxypalmitic acid palmityl ester | 0 |
| 2-isobutyloxymyristic acid- (18)-methylisaconyl ester | 0 |
| 2-acetyloxymyristic acid- (18)-methylnonadecanyl ester | 0 |
| 2-isobutyloxy long-chain fatty acid (14-25) long-chain branched alcohol (12-31) ester | 0 |
| 2-isobutyryloxypalmitic acid palmityl ester | 0 |
| 2-acetyloxypalmitic acid palmityl ester | 0 |
| 2-isovaleryloxypalmitic acid lauryl ester | 0 |
| 2-long-chain branched fatty acid (12-31) oxypalmitic acid palmiyl ester | 0 |
| Wax diesters of Cashmere | 0 |

As described in Table 2, it had been confirmed that the alpha-hydroxy fatty acid derivatives of the present invention had no irritation to the skin.

Application Example 1 and Comparative Example 1 (Skin Cream)

The skin creams were prepared with the formulation shown in Table 3 by a conventional method. Application Example 1 was a skin cream containing 2-palmitoyloxypalmitic acid palmityl ester obtained in Example 1. A skin care cream containing no alpha-hydroxy fatty acid derivatives as Comparative Example 1 was prepared. The comparative sensory test was carried out by applying the skin care creams of Application Example 1 and Comparative Example 1 to each lower leg portion of 20 women panelists twice a day for one week by a conventional method. The results of the comparative sensory test, the number of persons, who answered that "the skin became smooth", "the skin was moisturized" and "the skin was firmer" with respect to the respective items such as smoothness, moisture and elasticity, are also shown in Table 3.

TABLE 3

| | Application Example 1 | Comparative Example 1 |
|---|---|---|
| Name of Components (wt %) | | |
| 2-palmitoyloxypalmitic acid palmityl ester | 15.0 | — |
| Squalane | 5.0 | 5.0 |
| Liquid petrolatum | 5.0 | 5.0 |
| Cholesterol | 0.5 | 0.5 |
| Hydrogenated soybean phopholipid | 1.0 | 1.0 |
| Glyceryl monostearate | 1.0 | 1.0 |
| Sorbitan monostearate | 2.0 | 2.0 |
| Dipropylene glycol | 5.0 | 5.0 |
| 1,3-butylene glycol | 5.0 | 5.0 |
| Methyl parahydroxybenzoate | 0.1 | 0.1 |
| Purified water | balance | Balance |
| Comparative sensory test results (number of persons) | | |
| Smoothness | 19 | 1 |
| Moisture | 18 | 2 |
| Elasticity | 18 | 2 |

As shown in Table 3, the skin care cream of Application Example 1 as the skin composition of the present invention was superior in all properties to Comparative Example 1 which contains no alpha-hydroxy fatty acid derivative.

Application Example 1 had no problems in the stability and no skin trouble such as the irritation to skin.

Application Example 2 (Skin Care Milky Lotion)

A skin care milky lotion was prepared with the formulation of Table 4 using 2-isobutyryloxymyristic acid-(18)-methylicosanyl ester obtained in Example 2 and 2-acetyloxystearic acid-(18)-methylnonadecanyl ester obtained in Example 3 by a conventional method. The skin care milky lotion of the present invention exhibited an extremely good stability of emulsified state, and was not greasy and exhibited good affinity with the skin when applied on the face, hands and feet. Also the skin care milky lotion had excellent sensory properties capable of providing the smoothness, moisture and elasticity.

TABLE 4

| Name of components (wt %) | Application Example 2 |
|---|---|
| 2-isobutyloxymyristic acid- (18)-methylisaconyl ester | 3.0 |
| 2-acetyloxymyristic acid- (18)-methylnonadecanyl ester | 2.0 |
| Octyldodecy myristate | 2.0 |
| Poloxyethylene hydrogenated castor oil (60 E.O.) | 1.0 |
| Myristic acid | 0.5 |
| Glycerin | 10.0 |
| Diglycerin | 5.0 |
| Maltitol | 2.0 |
| Carboxyvinyl polymer | 0.2 |
| Potassium hydroxide | 0.3 |
| Methyl parahydroxybenzoate | 0.1 |
| Potassium edetate | 0.1 |
| Purified water | balance |

Application Example 3 (Lipstick)

A lipstick was prepared with the formulation of Table 5 using 2-acetyloxypalmitic acid palmityl ester obtained in Example 6, 2-long-chain branched fatty acid (12-31) oxypalmitic acid palmityl ester obtained in Example 8 and the wax diesters of Cashmere obtained in Example 9 by a conventional method. The lipstick as the skin composition of the present invention was good stability such as good dispersion of pigments and exhibited excellent sensory properties such as no greasiness and good make-up retention. The lipstick was prepared by using a Cashmere lipids extract of Example 9 in place of the wax diesters of Cashmere had slight odor as compared with the lipstick of Application Example 3, but exhibited excellent sensory properties.

TABLE 5

| Name of components (wt %) | Application Example 3 |
|---|---|
| 2-palmitoyloxypalmitic acid palmityl ester | 30.0 |
| 2-long-chain branched fatty acid (12-31) oxypalmitic acid palmityl | 20.0 |
| Wax diesters of Cashmere | 10.0 |
| Beeswax | 10.0 |
| Carnauba wax | 10.0 |
| 2-Octyldodecanol | 5.0 |
| Behenyl alcohol | 5.0 |
| Pigment | 9.8 |
| Perfume | 0.2 |

Application Example 4 and Comparative Example 2 (Hair Rinses)

A hair rinses were prepared with the formulation shown in Table 6 by a conventional method. Application Example 4 was a hair rinse containing 2-isobutyryloxy long-chain fatty acid (14–25) long-chain branched alcohol (12–3) ester obtained in Example 4. Comparative Example 2 was lacked alpha-hydroxy fatty acid derivatives. The comparative sensory test was carried out by applying the hair rinses of Application Example 4 and Comparative Example 2 to 20 women panelists once a day for three days by a conventional method. The results of the comparative sensory test, the number of persons, who answered that "the hair became smooth", "the hair was moisturized" and "the hair became glossy" with respect to the respective items such as smoothness, moisture and gloss are also shown in Table 6.

TABLE 6

|  | Application Example 4 | Comparative Example 2 |
|---|---|---|
| Name of Components (wt %) | | |
| 2-isobutyryloxy long-chain fatty acid (14-25) long-chain branched alcohol (12-31) ester | 2.0 | — |
| Cetyl alcohol | 3.0 | 3.0 |
| Stearyl trimethyl ammonium chloride | 1.5 | 1.5 |
| Polyoxyethylene cetyl ether (10 E.O.) | 1.0 | 1.0 |
| Glycerin | 5.0 | 5.0 |
| Methyl parahydroxybenzoate | 0.1 | 0.1 |
| Perfume (flesh floral compound perfume) | 0.3 | 0.3 |
| Purified water | balance | balance |
| Comparative sensory test results (number of persons) | | |
| Smoothness | 20 | 0 |
| Moisture | 18 | 2 |
| Gloss | 19 | 1 |

As shown in Table 6, the hair rinse of Application Example 4 as the hair composition of the present invention was superior in all properties to Comparative Example 2 which lacked the alpha-hydroxy fatty acid derivatives. Application Example 4 had no problem in the stability and no skin trouble such as the irritation to skin.

Application Example 5 (Hair Shampoo)

A hair shampoo was prepared with the formulation shown in Table 7 using 2-isovaleryloxylauric acid lauryl ester obtained in Example 7. The hair shampoo of Application Example 5 of the present invention exhibited satisfactory foaming and detergency and was smooth on washing-out, and also exhibited excellent sensory properties such as smoothness, moisture and gloss after drying.

TABLE 7

| Name of components (% by weight) | Application Example 5 |
|---|---|
| 2-isovaleryloxylauric acid lauryl ester | 0.1 |
| Lauramidopropyl betaine | 15.0 |
| Coconut fatty acid diethanolamide | 5.0 |
| Sodium N-cocoyl N-methyl tauratecoconut | 3.0 |
| Stearyl trimethyl ammonium chloride | 0.3 |
| Polyoxyethylene-methylpolysiloxane copolymer | 0.5 |
| Methyl parahydroxybenzoate | 0.2 |
| Citric acid | 0.2 |
| Disodium edetate | 0.1 |
| Perfume (citrus perfume) | 0.6 |
| Purified water | balance |

As described above, the novel alpha-hydroxy fatty acid derivatives of the present invention have excellent properties for oily base with low melting points and dose not irritation to the skin. Furthermore, skin and hair compositions containing the alpha-hydroxy fatty acid derivative as an essential component had good stability and also had good sensory properties. The novel composition of present invention is useful for external use.

What is claimed is:

1. A composition for external application comprising one of more compounds having the general formula (1):

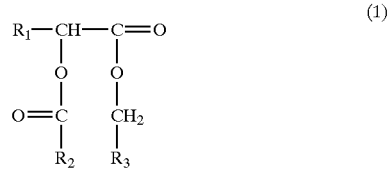

wherein
$R_1$ is selected from the group consisting of a linear alkyl group having 10 to 24 carbon atoms and a branched alkyl group having 10 to 24 carbon atoms,
$R_2$ is selected from the group consisting of a linear aklyl group having 1 to 31 carbon atoms and a branched alkyl group having 1 to 31 carbon atoms, and
$R_3$ is selected from the group consisting of a linear alkyl group having 11 to 31 carbon atoms and a branched alkyl group having 11 to 31 carbon atoms.

2. A composition for external application according to claim 1 wherein the compound(s) of formula (1) comprises from 0.1 to 60% by weight of the total amount of said composition.

3. A composition for external application according to claim 1 further comprising at least one additive selected from the group consisting of a surfactant, a polyhydric alcohol and a higher alcohol having 12 to 22 carbon atoms.

4. A composition for external application according to claim 1 further comprising at least one additive selected from the group consisting of perfumes and pigments.

5. A composition for external application according to claim 1 further comprising a viscosity modifiers.

6. A composition for external application according to claim 1 further comprising an additional oil or emollient.

7. A composition for external application according to claim 1, further comprising at least one additive selected from the group consisting of an antioxidant, a sunscreen agent and ultraviolet light absorber, a chelating agent, an inorganic salt, a vitamin, and a vegetable extract.

8. A composition for external application according to claim 1 wherein said compound(s) is at least one member selected from the group consisting of;

2-palmitoyloxypalmitic acid palmityl ester,
2-isobutyryloxymyristic acid-(18)-methylicosanyl ester,
2-acetyloxystearic acid-(18)-methylnonadecanyl ester,
2-isobutyloxy long-chain fatty acid (14–25) long-chain branched alcohol (12–31) ester,
2-isobutyryloxypalmitic acid palmityl ester,
2-acetyloxypalmitic acid palmityl ester,
2-isovaleryloxylauric acid lauryl ester,
and 2-long-chain branched fatty acid (12–31) oxypalmitic acid palmityl ester.

9. The composition according to claim 1, wherein said composition for external application is a cosmetic.

10. The composition according to claim 1, wherein said composition for external application is a pharmaceutical.

11. The composition according to claim 1, wherein said composition for external application is in the form of an oily base or an emulsion.

12. The composition according to claim 1, wherein said composition for external application is a lotion, a cream, a pack, a face wash, a foundation or a lipstick.

13. The composition according to claim 1, wherein said composition for external application is a bath preparation.

14. The composition according to claim 1, wherein said composition for external application is a hair composition.

15. A compound having the general formula (2):

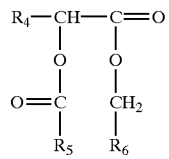

wherein $R_4$ is selected from the group consisting of a linear alkyl group having 10 to 20 carbon atoms and a branched alkyl group having 10 to 20 carbon atoms, $R_5$ is selected from the group consisting of a linear alkyl group having 1 to 5 carbon atoms and an iso- or anteiso-branched alkyl group having 1 to 5 carbon atoms, and $R_6$ is selected from the group consisting of a linear alkyl group having 11 to 31 carbon atoms and an iso- or anteiso-branched alkyl group having 11 to 31 carbon atoms.

16. A composition for external application comprising one or more compounds having the general formula (2):

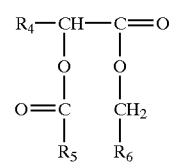

wherein $R_4$ is selected from the group consisting of a linear alkyl group having 10 to 20 carbon atoms and a branched alkyl group having 10 to 20 carbon atoms, $R_5$ is selected from the group consisting of a linear alkyl group having 1 to 5 carbon atoms and an iso- or anteiso-branched alkyl group having 1 to 5 carbon atoms, and $R_6$ is selected from the group consisting of a linear alkyl group having 11 to 31 carbon atoms and an iso- or anteiso-branched alkyl group having 11 to 31 carbon atoms.

* * * * *